United States Patent [19]

Kraatz et al.

[11] 4,427,672

[45] Jan. 24, 1984

[54] COMBATING FUNGI WITH SUBSTITUTED TRIAZOLYLALKYL PYRIDYL ETHERS

[75] Inventors: Udo Kraatz, Leverkusen; Jörg Stetter, Wuppertal; Karl H. Büchel, Burscheid; Paul-Ernst Frohberger, Leverkusen; Wilhelm Brandes, Leichlingen, all of Fed. Rep. of Germany

[73] Assignee: Bayer Aktiengesellschaft, Leverkusen, Fed. Rep. of Germany

[21] Appl. No.: 281,628

[22] Filed: Jul. 9, 1981

[30] Foreign Application Priority Data

Jul. 29, 1980 [DE] Fed. Rep. of Germany ....... 3028669

[51] Int. Cl.³ .................... A01N 43/64; A01N 59/16; C07D 401/12; C07F 1/08
[52] U.S. Cl. .............................. 424/245; 260/456 R; 424/232; 424/263; 546/2; 546/8; 546/9; 546/276; 546/288; 546/296; 546/301; 546/302; 546/303; 548/262; 568/419
[58] Field of Search ..................... 546/2, 8, 9, 276; 424/232, 245, 263

[56] References Cited

U.S. PATENT DOCUMENTS

| 4,166,854 | 9/1979 | Carson et al. | 546/276 |
| 4,255,434 | 3/1981 | Kramer et al. | 424/269 |

FOREIGN PATENT DOCUMENTS

| 2678 | 7/1979 | European Pat. Off. . |
| 32561 | 7/1981 | European Pat. Off. . |
| 2535332 | 2/1977 | Fed. Rep. of Germany . |
| 2552967 | 6/1977 | Fed. Rep. of Germany . |
| 55-28923 | 2/1980 | Japan | 546/276 |

*Primary Examiner*—Alton D. Rollins
*Attorney, Agent, or Firm*—Sprung Horn Kramer & Woods

[57] ABSTRACT

Substituted triazolylalkyl pyridyl ethers of the formula

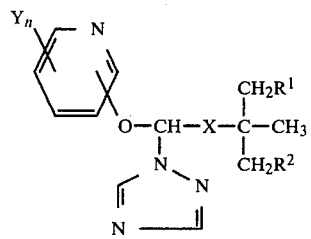

in which
  $R^1$ is a halogen atom,
  $R^2$ is a hydrogen or halogen atom,
  X is a keto group or a CH(OH) group,
  Y each independently is a halogen atom or an alkyl, alkoxy or cyano group, and
  n is 0, 1, 2, 3 or 4, or an addition product thereof with a physiologically acceptable acid or metal salt which possesses fungicidal activity. Intermediates therefor wherein X is a keto group and with a halogen atom in place of either the pyridinyloxy group or the azole group are also new.

10 Claims, No Drawings

COMBATING FUNGI WITH SUBSTITUTED TRIAZOLYLALKYL PYRIDYL ETHERS

The present invention relates to certain new substituted triazolylalkyl pyridyl ethers, to several processes for their production and to their use as fungicides.

It has already been disclosed that certain 3,3-dimethyl-1-pyridyloxy-1-triazolyl-butan-2-ones have a good fungicidal activity (see our U.S. application Ser. No. 964,768, filed Nov. 29, 1978 now U.S. Pat. No. 4,396,624). However, their action is not always completely satisfactory, especially when low amounts and concentrations are applied.

The present invention now provides, as new compounds, the substituted triazolylalkyl pyridyl ethers of the general formula

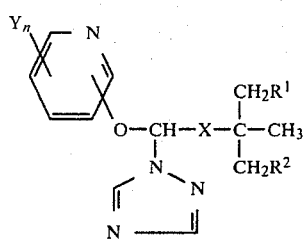

(I)

in which
- $R^1$ represents a halogen atom,
- $R^2$ represents a hydrogen or halogen atom,
- X represents a keto group or a CH(OH) grouping, each
- Y independently represents a halogen atom or an alkyl, alkoxy or cyano group and
- n is 0, 1, 2, 3 or 4, and physiologically acceptable acid addition salts and metal salt complexes thereof.

Those compounds of the formula (I) in which X represents the CH(OH) group have two asymmetric carbon atoms; they can therefore exist in the form of the two geometric isomers (erythro-form and threo-form), which can be obtained in varying proportions. In both cases, they are in the form of optical isomers. All the isomers are claimed according to the invention.

According to the present invention there is further provided a process for the production of a substituted triazolylalkyl pyridyl ether of the present invention in which (a) a triazolyl-halogenoketone of the general formula

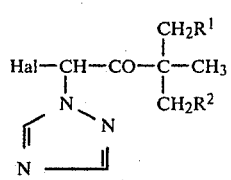

(II)

in which
- $R^1$ and $R^2$ have the abovementioned meanings and
- Hal represents a chlorine or bromine atom, is reacted with a pyridinol of the general formula

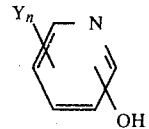

(III)

in which Y and n have the abovementioned meaning, in the presence of an acid-binding agent and in the presence of a diluent, or (b) a halogenoether-ketone of the general formula

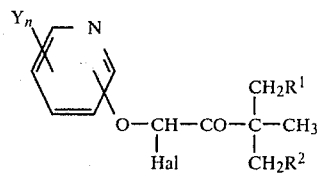

(IV)

in which Hal, $R^1$, $R^2$, Y and n have the abovementioned meanings, is reacted with 1,2,4-triazole in the presence of an acid-binding agent, and if appropriate in the presence of a diluent; or (c), where a compound of formula (I) is required in which X represents a CH(OH) grouping, a keto derivative obtained by process variant (a) or (b), of the general formula

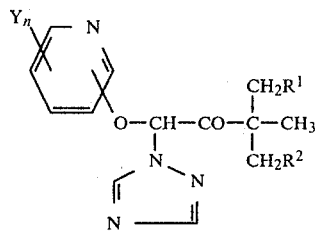

(Ia)

in which $R^1$, $R^2$, Y and n have the abovementioned meanings, is reduced; and the acid or metal salt is then, if desired, added onto the compound of the formula (I) obtained by process variant (a) (b) or (c).

The new substituted triazolyl pyridyl ethers of the present invention have powerful fungicidal properties. Surprisingly, the compounds according to the invention exhibit a better fungicidal activity than the 3,3-dimethyl-1-pyridyloxy-1-triazolyl-butan-2-ones which are known from the state of the art and are the most closely related compounds chemically and from the point of view of their action. The substances according to the invention thus represent an enrichment of the art.

Preferred substituted triazolyl pyridyl ethers of the present invention are those in which $R^1$ represents a fluorine or chlorine atom and $R^2$ represents a hydrogen atom, or $R^1$ and $R^2$ are identical and denote fluorine or chlorine atoms, each Y independently represents a hydrogen atom or a straight-chain or branched alkyl or alkoxy group with in each case 1 to 4 carbon atoms or a cyano group and X and n have the abovementioned meanings.

If n assumes a numerical value from 2 to 4, as indicated above, radicals Y can have the same or different meanings.

If, for example, 1-bromo-3,3-dimethyl-4-fluoro-1-(1,2,4-triazol-1-yl)-butan-2-one and 6-chloro-pyridin-2-ol are used as starting substances, the course of process variant (a) according to the present invention is illustrated by the following equation:

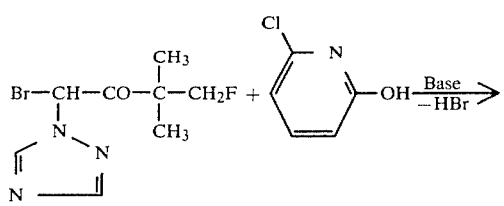

If, for example, 1-bromo-1-(6-chloro-pyridin-2-yl-oxy)-3,3-dimethyl-4-fluoro-butan-2-one and 1,2,4-triazole are used as starting substances, the course of process variant (b) according to the present invention is illustrated by the following equation:

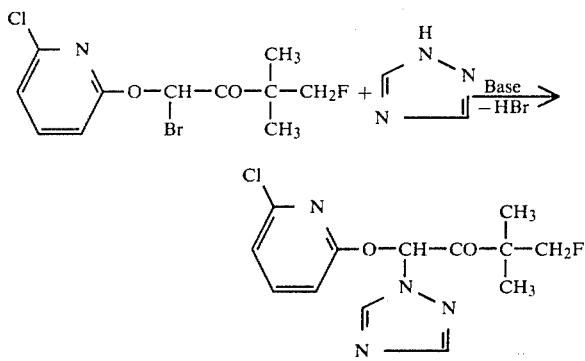

If, for example, 1-(6-chloro-pyridin-2-yl-oxy)-3,3-dimethyl-4-fluoro-1-(1,2,4-triazol-1-yl)-butan-2-one and sodium borohydride are used as starting substances, the course of process variant (c) according to the present invention is illustrated by the following equation:

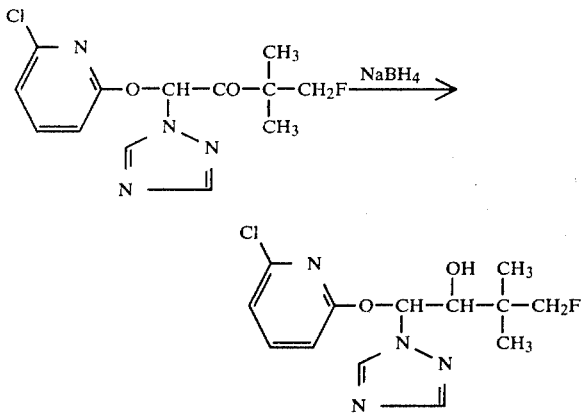

Preferred triazolyl-halogenoketones of formula (II) to be used as starting substances for process variant (a) are those in which $R^1$ and $R^2$ represent the radicals which have already been mentioned in connection with the description of the preferred compounds according to the invention.

The triazolyl-halogenoketones of the formula (II) are novel; however, they can be obtained in a generally known manner, by a process in which a halide of the formula

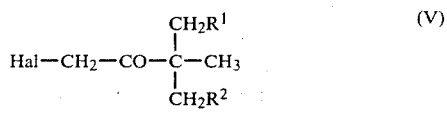

in which $R^1$, $R^2$ and Hal have the abovementioned meaning, is reacted with 1,2,4-triazole in the presence of an acid-binding agent (such as potassium carbonate), and in the presence of an inert organic solvent (such as acetone), at a temperature between 60° and 120° C. One of the two active hydrogen atoms is then replaced by chlorine or bromine in the customary manner. The triazolyl-halogenoketones of the formula (II) can be further reacted directly.

The halides of the formula (V) are known (see our DE-OS (German Published Specification) No. 2,632,603 and our DE-OS (German Published Specification) No. 2,843,767).

Starting substances of the formula (II) which may be mentioned are: 1-bromo(chloro)-3,3-dimethyl-4-fluoro-1-(1,2,4-triazol-1-yl)-butan-2-one, 1-bromo(chloro)-4-chloro-3,3-dimethyl-1-(1,2,4-triazol-1-yl)-butan-2-one, 3,3-bis-fluoromethyl-1-bromo(chloro)-1-(1,2,4-triazol-1-yl)-butan-2-one and 3,3-bischloromethyl-1-bromo(chloro)-1-(1,2,4-triazol-1-yl)-butan-2-one.

Preferred pyridinols of formula (III) to be used as starting substances for process variant (a) and those in which Y and n have the meanings already mentioned in connection with the description of the preferred compounds according to the invention. If appropriate, the pyridinols of the formula (III) are also employed in the form of their silver salts.

The pyridinols of the formula (III) are generally known compounds of organic chemistry. Examples which may be mentioned are: 2-hydroxy-pyridine, 3-hydroxy-pyridine, 4-hydroxy-pyridine, 2-hydroxy-6-chloro-pyridine, 3-hydroxy-5-chloro-pyridine, 2-hydroxy-4-chloro-pyridine, 2-hydroxy-3-chloro-pyridine, 2-hydroxy-6-bromo-pyridine, 2-hydroxy-5-bromo-pyridine, 2-hydroxy-4-bromo-pyridine, 2-hydroxy-3-bromo-pyridine, 2-hydroxy-6-methyl-pyridine, 2-hydroxy-5-methyl-pyridine, 2-hydroxy-4-methyl-pyridine, 2-hydroxy-3-methyl-pyridine, 2-hydroxy-6-fluoro-pyridine, 2-hydroxy-5-fluoro-pyridine, 2-hydroxy-4-fluoro-pyridine, 2-hydroxy-3-fluoro-pyridine, 3-hydroxy-2-chloro-pyridine, 3-hydroxy-2-bromo-pyridine, 3-hydroxy-2-fluoro-pyridine, 3-hydroxy-2-iodo-pyridine, 3-hydroxy-2-methoxy-pyridine, 3-hydroxy-6-chloro-pyridine, 3-hydroxy-5-chloro-pyridine, 4-hydroxy-2-chloro-pyridine, 4-hydroxy-pyridine, 4-hydroxy-3-chloro-pyridine, 2-hydroxy-3,5,6-trichloro-pyridine, 2-hydroxy-3-cyano-5,6-dichloro-4-methyl-pyridine, 2-hydroxy-5-bromo-6-chloro-pyridine, 2-hydroxy-5-chloro-4,6-dimethyl-3-cyano-pyridine, 2-hydroxy-3,5-dichloro-pyridine, 2-hydroxy-5-bromo-4,6-dimethyl-3-cyano-pyridine, 3-hydroxy-2,6-diiodopyridine, 2-hydroxy-3,5-dibromo-6-chloro-pyridine and 2-hydroxy-5-bromo-6-chloro-3-cyano-4-methylpyridine.

Preferred halogenoether-ketones of formula (IV) to be used as starting substances for process variant (b) are those in which $R^1$, $R^2$ Y and n have the meanings which have already been mentioned in connection with the description of the preferred compounds according to the invention.

The halogenoether-ketones of the formula (IV) are novel; however, they can be prepared by known processes, by reacting a pyridinol of the formula (III) with a halide of the formula (V) in the presence of an acid-binding agent (such as potassium carbonate), and in the presence of an inert organic solvent (such as acetone), at a temperature between 60° and 120° C. One of the two active hydrogen atoms is then replaced by chlorine or bromine in the customary manner.

Possible diluents for the reactions, according to the invention, in process variants (a) and (b) are inert organic solvents. These include, preferably, ketones (such as diethyl ketone, and, preferably, acetone and methyl ketone), nitriles (such as propionitrile, and, preferably acetonitrile), alcohols (such as ethanol or isopropanol), ethers (such as tetrahydrofuran or dioxane), benzene, formamides (such as, preferably, dimethylformamide) and halogenated hydrocarbons.

The reactions of processes (a) and (b) are carried out in the presence of an acid-binding agent. It is possible to add any of the inorganic or organic acid-binding agents which can customarily be used, such as alkali metal carbonates (for example sodium carbonate, potassium carbonate and sodium bicarbonate) or such as silver carbonate, or such as tertiary alkylamines, cycloalkylamines or aralkylamines having up to 7 carbon atoms per alkyl or cycloalkyl radical (for example triethylamine or dimethylbenzylamine), or such as pyridine and diazabicyclooctane. In process variant (b), it is also possible to use an appropriate excess of 1,2,4-triazole.

The reaction temperatures can be varied within a substantial range in process variants (a) and (b). In general, the reactions are carried out at a temperature between 20° and 150° C., preferably between 60° and 120° C. If a solvent is present, it is expedient to carry out the reaction at the boiling point of the particular solvent.

In carrying out process variant (a) or (b) according to the invention, generally 1 to 2 moles of pyridinol of the formula (III) or 1 to 2 moles of azole and in each case 1 to 2 moles of acid-binding agent are employed per mole of the compound of the formula (II) or (IV). In order to isolate the compound of the formula (I), the solvent is distilled off, and the residue is either treated with water and stirred vigorously, whereupon the reaction product crystallizes completely, or the residue is taken up in a mixture of an organic solvent and water and the organic phase is separated off, washed with water, dried over sodium sulphate and freed from the solvent in vacuo. If appropriate, the residue is purified by distillation or recrystallization.

The reduction, according to the invention, in process variant (c) is carried out in the customary manner, for example by reaction with complex hydrides, if appropriate in the presence of a diluent, or by reaction with aluminum isopropylate in the presence of a diluent.

If complex hydrides are used, possible diluents for the reaction according to the invention are polar organic solvents. These include, preferably, alcohols, (such as methanol, ethanol, butanol or isopropanol) and ethers (such as diethyl ether or tetrahydrofuran). The reaction is in general carried out at a temperature between 0° and 30° C., preferably at between 0° and 20° C. For this reaction, generally about 1 mole of a complex hydride (such as sodium hydride or lithium alanate) is employed per mole of the ketone of the formula (Ia). To isolate the reduced compounds of the formula (I), the residue is taken up in dilute hydrochloric acid and the mixture is then rendered alkaline and extracted with an organic solvent. Further working up is effected in the customary manner.

If aluminum isopropylate is used, preferred possible diluents for the reaction according to the invention are alcohols (such as isopropanol) or inert hydrocarbons (such as benzene). The reaction temperatures can again be varied within a substantial range; in general, the reaction is carried out at a temperature between 20° and 120° C., preferably between 50° and 100° C. For carrying out the reaction, about 1 to 2 moles of aluminum isopropylate are employed per mole of the ketone of the formula (Ia). To isolate the reduced compounds of the formula (I), the excess solvent is removed by distillation in vacuo and the aluminum compound formed is decomposed with dilute sulphuric acid or sodium hydroxide solution. Further working up is effected in the customary manner.

The following acids can preferably be used for the preparation of physiologically acceptable acid addition salts of the compounds of the present invention: hydrogen halide acids (such as hydrobromic acid, and, preferably, hydrochloric acid), phosphoric acid, nitric acid, sulphuric acid, monofunctional and bifunctional carboxylic acids and hydroxycarboxylic acids (such as acetic acid, maleic acid, succinic acid, fumaric acid, tartaric acid, citric acid, salicylic acid, sorbic acid and lactic acid) and sulphonic acids (such as p-toluenesulphonic acid and 1,5-naphthalenedisulphonic acid).

The acid addition salts of the compounds of the formula (I) can be obtained in a simple manner by customary salt formation methods, for example by dissolving a compound of the formula (I) in a suitable inert solvent and adding the acid, for example hydrogen chloride, and they can be isolated in a known manner, for example by filtration, and if appropriate purified by washing with an inert organic solvent.

Salts of metals of main groups II to IV and of subgroups I and II and IV to VIII are preferably used for the preparation of metal salt complexes of the compounds of the formula (I), examples of metals which may be mentioned being copper, zinc, manganese, magnesium, tin, iron and nickel.

Possible anions of the salts are, preferably, those which are derived from the following acids: hydrogen halide acids, such as hydrochloric acid and hydrobromic acid, and furthermore phosphoric acid, nitric acid and sulphuric acid.

The metal salt complexes of the compounds of the formula (I) can be obtained in a simple manner by customary processes, thus, for example, by dissolving the metal salt in alcohol, for example ethanol, and adding the solution to the compound of the formula (I). The metal salt complexes can be purified in a known manner, for example by filtration, isolation, and, if appropriate, by recrystallization.

The active compounds according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants, of the active compounds, at the concentrations required for combating plant diseases, permits treatment of above-ground parts of plants, of vegetative propagation stock and seeds, and of the soil.

As plant protection agents, the active compounds according to the invention can be used with particularly good success for combating cereal diseases, such as powdery mildew of cereal and powdery mildew of barley, Venturia species, such as against the apple scab causative organism (*Fusicladium dendriticum*), and rice diseases, such as against *Pellicularia sasakii*. It should be particularly emphasized that the active compound according to the invention not only have a protective action, but is some cases also have a systemic action. Thus, it is possible to protect plants from fungal attack if the active compound is fed to the above-ground parts of the plants via the soil and the root or via the seed.

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts or iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in the formulations or in the various use forms as a mixture with other known active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They are used in the customary manner, for example by watering, immersion, spraying, atomizing, misting, vaporizing, injecting, forming a slurry, brushing on, dusting, scattering, dry dressing, moist dressing, wet dressing, slurry dressing or encrusting.

Especially in the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g are generally required.

For the treatment of soil, active compound concentrations of 0.00001 to 0.1% by weight, preferably 0.0001 to 0.02%, are generally required at the place of action.

The present invention also provides a fungicidal composition containing as active ingredient a compound of the present invention in admixture with a solid or liquefied gaseous diluent or carrier or in admixture with a liquid diluent or carrier containing a surface-active agent.

The present invention also provides a method of combating fungi which comprises applying to the fungi, or to a habitat thereof, a compound of the present invention alone or in the form of a composition containing as active ingredient a compound of the present invention in admixture with a diluent or carrier.

The present invention further provides crops protected from damage by fungi by being grown in areas in which immediately prior to and/or during the time of the growing a compound of the present invention was applied alone or in admixture with a diluent or carrier.

PREPARATIVE EXAMPLES

Example 1

(process variant (a))

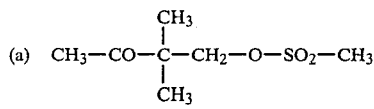

232 g (2 moles) of 3,3-dimethyl-4-hydroxy-2-butanone (for the preparation, see Beilstein H 1 E III 3239, IV 4030 and Bull. Soc. Chim.France 1964, 2849) were reacted with 229 g (2 moles) of methanesulphonyl chloride in 700 ml of absolute pyridine at 0° to 5° C. After leaving the mixture to stand at 20° C. for 12 hours, it was diluted with methylene chloride and extracted by shaking with ice-water. The organic phase was dried, and freed from the solvent in vacuo, and the residue was fractionated over a column. 332 g (that is to say 86% of theory) of 2,2-dimethyl-3-oxo-butyl methanesulphonate were isolated at a boiling point$_{0.12}$ of 106° to 120° C.

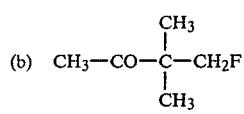

38.8 g (0.2 mole) of 2,2-dimethyl-3-oxobutyl methanesulphonate were added dropwise to a suspension, in a three-necked stirred flask with a descending condenser, of 23.2 g (0.4 mole) of dry potassium fluoride in 400 ml of distilled tetraethylene glycol at 160° C. and under 20 mbars in the course of 2 hours, and the mixture was subsequently stirred for a further 2 hours. The reaction product which had distilled out was condensed in a descending condenser and collected in a subsequent low-temperature trap. 20.9 g (0.177 mole, that is to say 89% of theory) of 3,3-dimethyl-4-fluoro-2-butanone, which had a boiling point of 130° C. to 134° C. under normal pressure, were thus obtained.

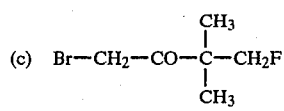

480 g of bromine were slowly added dropwise to a mixture of 354 g (3 moles) of 3,3-dimethyl-4-fluoro-2-butanone and 2,000 ml of ether at 20° to 30° C., while cooling and stirring. The yellowish solution was subsequently stirred at 20° C. for a further hour, and 500 ml of water were then carefully added. The ether phase was separated off, washed several times with water and dried over sodium sulphate. After distilling off the solvent, the residue was distilled under a waterpump vacuum. 472 g (80% of theory) of 1-bromo-3,3-dimethyl-4-fluoro-2-butanone of boiling point 80° to 90° C./11 mm Hg column were obtained.

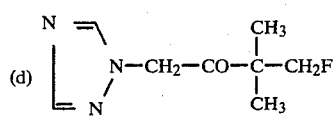

197 g (1 mole) of 1-bromo-3,3-dimethyl-4-fluoro-2-butanone were slowly added dropwise to a boiling solution of 77 g (1.1 mols) of 1,2,4-triazole and 210 g (1.5 moles) of potassium carbonate in 500 ml of acetone such that, after removing the heating bath, the exothermic reaction kept the solution simmering. The mixture was then kept under reflux for a further 3 hours, the inorganic salts were filtered off and the filtrate was concentrated in vacuo. The residue was taken up in chloroform/water and the organic phase was separated off and evaporated. The residue which remained was distilled in vacuo and the distillate was crystallized with cyclohexane. 112 g (55% of theory) of 3,3-dimethyl-4-fluoro-1-(1,2,4-triazol-1-yl)-butan-2-one of melting point 59° C. were obtained.

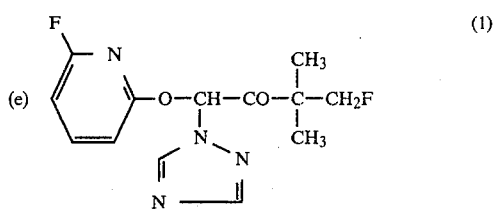

(process variant (a))

18.5 g (0.1 mole) of 3,3-dimethyl-4-fluoro-1-(1,2,4-triazol-1-yl)-butan-2-one were dissolved in 150 ml of glacial acetic acid, and, after adding 8.2 g (0.1 mole) of sodium acetate, 16 g (0.1 mole) of bromine were added dropwise at 45° C., until the mixture was completely decolorized. The mixture was then poured into ice-water and extracted with chloroform. The combined chloroform extracts were washed with sodium bicarbonate solution, dried over magnesium sulphate and concentrated. The oily 1-bromo-3,3-dimethyl-4-fluoro-1-(1,2,4-triazol-1-yl)-butan-2-one which remained was dissolved in 50 ml of acetonitrile, and 11.3 g (0.1 mole) of 6-fluoro-2-hydroxy-pyridine and 10.5 g (0.1 mole) of triethylamine, both dissolved in 120 ml of acetonitrile, were added, while stirring. The mixture was stirred under reflux for 1 hour. It was then concentrated by distilling off the solvent in vacuo, and the residue was stirred with water. The crystalline precipitate formed was filtered off and recrystallized from cyclohexane. 20 g (68% of theory) of 3,3-dimethyl-4-fluoro-1-(6-fluoro-pyridin-2-yl-oxy)-1-(1,2,4-triazol-1-yl)-butan-2-one of melting point 116° C. were obtained.

(Process variant (c))

Example 2

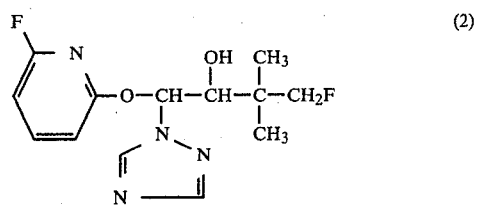

10 g (34 m moles) of 3,3-dimethyl-4-fluoro-1-(6-fluoro-pyridin-2-yl-oxy)-1-(1,2,4-triazol-1-yl)-butan-2-one (obtained as described in Example 1) were dissolved in 100 ml of methanol, and 0.7 g (17 m moles) of sodium borohydride was added. The mixture was stirred under reflux for 10 minutes and concentrated and the residue was partitioned between methylene chloride/water. The organic phase was separated off, washed with water, dried over sodium sulphate and concentrated. 9.3 g (90% of theory) of waxy 3,3-dimethyl-4-fluoro-1-(6-fluoro-pyridin-2-yl-oxy)-1-(1,2,4-triazol-1-yl)-butan-2-ol were obtained.

The following compounds of the general formula

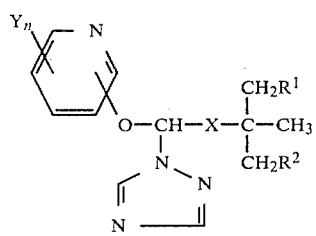

were obtained analogously, and according to process variants (a), (b) and (c).

| Compound No. | Y_n–pyridyl | X | R¹ | R² | Melting point (°C.) |
|---|---|---|---|---|---|
| 3 | pyridin-2-yl | CO | F | H | 62 |
| 4 | 5-Cl-pyridin-2-yl | CO | F | H | 108–110 |
| 5 | 3,5-Cl₂-pyridin-2-yl | CO | F | H | 102–104 |
| 6 | 5,6-Cl₂-3-CH₃-4-CN-pyridin-2-yl | CO | F | H | 120 |
| 7 | 4,6-Cl₂-pyridin-2-yl | CO | F | H | 136 |
| 8 | 5-Br-4,6-(CH₃)₂-3-CN-pyridin-2-yl | CO | F | H | 153 |
| 9 | 6-Cl-3-CH₃-4-CN-pyridin-2-yl | CO | F | H | 105 |
| 10 | 6-Cl-pyridin-2-yl | CO | Cl | H | 63–65 |
| 11 | pyridin-2-yl | CO | Cl | H | 58 |
| 12 | 6-F-pyridin-2-yl | CO | Cl | H | 89 |
| 13 | 5-Cl-pyridin-2-yl | CO | Cl | H | 100 |
| 14 | 3,5,6-Cl₃-pyridin-2-yl | CO | Cl | H | 126 |
| 15 | 3-I-pyridin-2-yl | CO | F | H | 100 |
| 16 | 3-Br-pyridin-2-yl | CO | F | H | 88 |
| 17 | 3-Cl-pyridin-2-yl | CO | F | H | Oil |
| 18 | 3-Cl-pyridin-2-yl | CO | Cl | H | Oil |

-continued

| Compound No. | Pyridinyl group | X | R¹ | R² | Melting point (°C.) |
|---|---|---|---|---|---|
| 19 | 3,5,6-trichloropyridin-2-yl | CH(OH) | F | H | 78 |
| 20 | 5-chloro-3-cyano-4,6-dimethylpyridin-2-yl | CH(OH) | F | H | 171 |
| 21 | 5-bromo-3-cyano-4,6-dimethylpyridin-2-yl | CH(OH) | F | H | 176 |
| 22 | 6-chloropyridin-2-yl | CH(OH) | Cl | H | Oil |
| 23 | 6-chloropyridin-2-yl | CH(OH) | F | H | Oil |
| 24 | 3,5,6-trichloropyridin-2-yl | CH(OH) | Cl | H | 135–137 |
| 25 | 2-chloropyridin-3-yl | CH(OH) | F | H | 110–120 |
| 26 | 2-chloropyridin-3-yl | CH(OH) | Cl | H | 108–118 |
| 27 | pyridin-2-yl | CO | F | F | 54 |
| 28 | 5-chloropyridin-2-yl | CO | F | F | 101–106 |
| 29 | 6-chloropyridin-2-yl | CO | F | F | 76 |
| 30 | 6-fluoropyridin-2-yl | CO | F | F | 100 |
| 31 | 5,6-dichloro-3-cyano-4-methylpyridin-2-yl | CO | F | F | 126 |
| 32 | 3,5,6-trichloropyridin-2-yl | CO | F | F | 136 |
| 33 | 5-chloro-3-cyano-4,6-dimethylpyridin-2-yl | CO | F | F | 110 |
| 34 | pyridin-2-yl | CO | Cl | Cl | Oil |
| 35 | 6-chloropyridin-2-yl | CO | Cl | Cl | 65 |
| 36 | 6-fluoropyridin-2-yl | CO | Cl | Cl | 76 |
| 37 | 5-chloropyridin-2-yl | CO | Cl | Cl | 98 |
| 38 | pyridin-3-yl | CO | F | F | Oil |

-continued

| Compound No. | ![structure] | X | R¹ | R² | Melting point (°C.) |
|---|---|---|---|---|---|
| 39 | (2-iodo-pyridyl) | CO | F | F | 82 |
| 40 | (2-bromo-pyridyl) | CO | F | F | 45 |
| 41 | (2-fluoro-pyridyl) | CH(OH) | F | F | 102–106 |
| 42 | (trichloro-pyridyl) | CH(OH) | F | F | 140–142 |
| 43 | (2-fluoro-pyridyl) | CH(OH) | Cl | Cl | Resin |
| 44 | (pyridyl) | CH(OH) | Cl | Cl | Resin |

The fungicidal activity of the compounds of this invention is illustrated by the following biotest examples.

In these examples, the compounds according to the present invention are each identified by the number (given in brackets) from the corresponding preparative examples and table hereinabove.

The known comparison compounds are identified as follows:

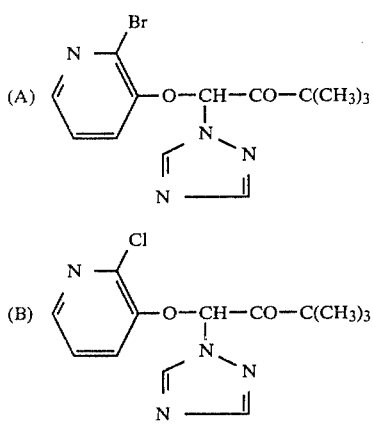

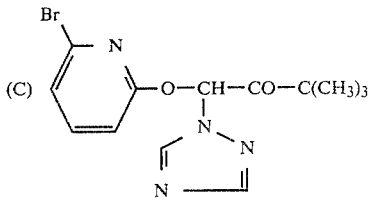

Example 3

Erysiphe test (barley)/protective
Solvent: 100 parts by weight of dimethylformamide
Emulsifier: 0.25 part by weight of alkylaryl polyglycol ether To produce a suitable preparation of active compound, 1 part by weight of active compound was mixed with the stated amounts of solvent and emulsifier, and the concentrate was diluted with water to the desired concentration.

To test for protective activity, young plants were sprayed with the preparation of active compound until dew-moist. After the spray coating had dried on, the plants were dusted with spores of *Erysiphe graminis f.sp. hordei.*

The plants were placed in a greenhouse at a temperature of about 20° C. and a relative atmospheric humidity of about 80%, in order to promote the development of powdery mildew pustules.

Evaluation was carried out 7 days after the inoculation.

In this test, a significantly superior activity compared with the prior art was shown, for example, by the following compounds: (1), (3), (4), (15), (16), (5), (10), (27), (28), (29), (30), (31), (32), (38), (39), (40), (2), (23), (25), (20), (22) and (26).

Example 4

Powdery mildew of barley test (*Erysiphe graminis var. hordei*)/systemic (fungal disease of cereal shoots)

The active compounds were used as pulverulent seed treatment agents. These were produced by extending the active compound with a mixture of equal parts by weight of talc and kieselguhr to give a finely pulverulent mixture of the desired concentration of active compound.

For the treatment of seed, barley seed was shaken with the extended active compound in a closed glass bottle. The seed was sown at the rate of 3×12 grains in flowerpots, 2 cm deep in a mixture of one part by volume of Fruhstorfer standard soil and one part by volume of quartz sand. The germination and emergence took place under favorable conditions in a greenhouse. 7 days after sowing, when the barley plants had unfolded their first leaf, they were dusted with fresh spores of *Erysiphe graminis var. hordei* and grown on at 21°–22° C. and 80–90% relative atmospheric humidity and 16 hours' exposure to light. The typical mildew pustules formed on the leaves within 6 days.

The degree of infection was expressed as a percentage of the infection of the untreated control plants. Thus, 0% denoted no infection and 100% denoted the same degree of infection as in the case of the untreated control. The more active was the active compound, the lower was the degree of mildew infection.

In this test, a significantly superior activity compared with the prior art was shown, for example, by the following compounds: (1), (5), (17), (10) and (23).

Example 5

Fusicladium test (apple)/protective
Solvent: 4.7 parts by weight of acetone
Emulsifier: 0.3 part by weight of alkylaryl polyglycol ether
Water: 95.0 parts by weight The amount of active compound required for the desired concentration of the active compound in the spray liquid was mixed with the stated amount of solvent, and the concentrate was diluted with the stated amount of water which contains the stated additions.

Young apple seedlings in the 4 to 6 leaf stage were sprayed with the spray liquid until dripping wet. The plants remained in a greenhouse for 24 hours at 20° C. and at a relative atmospheric humidity of 70%. They were then inoculated with an aqueous conidium suspension of the apple scab causative organism (*Fusicladium dendriticum*) and incubated for 18 hours in a humidity chamber at 18° to 20° C. and at a relative atmospheric humidity of 100%.

The plants then again came into a greenhouse for 14 days.

15 days after inoculation, the infection of the seedlings was determined. The assessment data obtained were converted to percent infection. 0% denoted no infection and 100% denoted that the plants were totally infected.

In this test, a significantly superior activity compared with the prior art was shown, for example, by the following compounds: (1), (22), (23) and (17).

It will be appreciated that the instant specification and examples are set forth by way of illustration and not limitation, and that various modifications and changes may be made without departing from the spirit and scope of the present invention.

We claim:

1. A substituted triazolylalkyl pyridyl ether of the formula

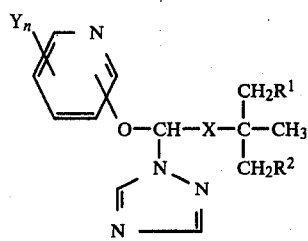

in which
   $R^1$ is a halogen atom,
   $R^2$ is hydrogen or halogen atom,
   X is a keto group or a CH(OH) group,
   Y each independently is a halogen atom, an alkyl or alkoxy group with 1 to 4 carbon atoms, or a cyano group, and
   n is 0, 1, 2, 3 or 4,
or an addition product thereof with a physiologically acceptable acid or metal salt.

2. A compound or addition product thereof according to claim 1, in which
   $R^1$ is a fluorine or chlorine atom, and
   $R^2$ is a hydrogen, fluorine or chlorine atom, or an addition product thereof with a physiologically acceptable hydrogen halide acid, phosphoric acid, nitric acid, sulphuric acid, monofunctional or bifunctional carboxylic acid, hydroxycarboxylic acid or sulphonic acid, or with a metal salt in which the metal is copper, zinc, manganese, magnesium, tin, iron or nickel and the anion is derived from hydrochloric, hydrobromic, phosphoric, nitric or sulphuric acid.

3. A compound according to claim 1, wherein such compound is 3,3-dimethyl-4-fluoro-1-(6-chloro-pyridin-2-yl-oxy)-1-(1,2,4-triazol-1-yl)-butan-2-ol of the formula

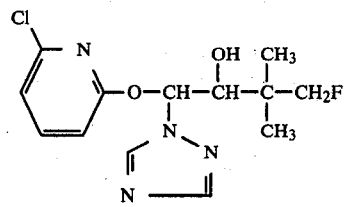

or an addition product thereof with a physiologically acceptable acid or metal salt.

4. A compound according to claim 1, wherein such compound is 3,3-bis-(fluoromethyl)-1-(5-chloro-pyridin-2-yl-oxy)-1-(1,2,4-triazol-1-yl)-butan-2-one of the formula

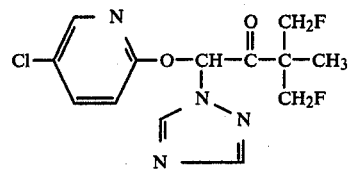

or an addition product thereof with a physiologically acceptable acid or metal salt.

5. A compound according to claim 1, wherein such compound is 3,3-bis-(fluoromethyl)-1-(6-chloro-pyridin-2-yl-oxy)-1-(1,2,4-triazol-1-yl)-butan-2-one of the formula

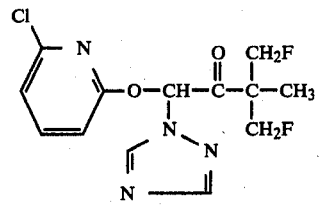

or an addition product thereof with a physiologically acceptable acid or metal salt.

6. A compound according to claim 1, wherein such compound is 3,3-bis-(chloromethyl)-1-(6-chloro-pyridin-2-yl-oxy)-1-(1,2,4-triazol-1-yl)-butan-2-one of the formula

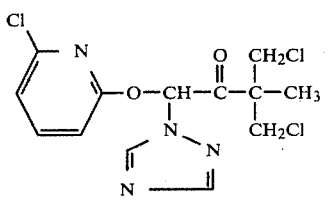

or an addition product thereof with a physiologically acceptable acid or metal salt.

7. A compound according to claim 1, wherein such compound is 3,3-bis-(chloromethyl)-1-(6-fluoro-pyridin-2-yl-oxy)-1-(1,2,4-triazol-1-yl)-butan-2-one of the formula

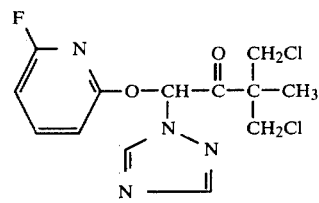

or an addition product thereof with a physiologically acceptable acid or metal salt.

8. A fungicidal composition comprising a fungicidally effective amount of a compound according to claim 1 in admixture with a diluent.

9. A method of combating fungi comprising applying to the fungi or to a habitat thereof, a fungicidally effective amount of a compound according to claim 1.

10. The method according to claim 9, wherein such compound is
3,3-dimethyl-4-fluoro-1-(6-chloro-pyridin-2-yl-oxy)-1-(1,2,4-triazol-1-yl)-butan-2-ol,
3,3-bis-(fluoromethyl)-1-(5-chloro-pyridin-2-yl-oxy)-1-(1,2,4-triazol-1-yl)-butan-2-one,
3,3-bis-(fluoromethyl)-1-(6-chloro-pyridin-2-yl-oxy)-1-(1,2,4-triazol-1-yl)-butan-2-one
3,3-bis-(chloromethyl)-1-(6-chloro-pyridin-2-yl-oxy)-1-(1,2,4-triazol-1-yl)-butan-2-one or
3,3-bis-(chloromethyl)-1-(6-fluoro-pyridin-2-yl-oxy)-1-(1,2,4-triazol-1-yl)-butan-2-one,
or an addition product thereof with a physiologically acceptable acid or metal salt.

* * * * *